United States Patent
Woehr et al.

(10) Patent No.: US 7,214,211 B2
(45) Date of Patent: May 8, 2007

(54) NEEDLE ASSEMBLY WITH PROTECTIVE ELEMENT

(75) Inventors: Kevin Woehr, Felsberg (DE); Jurgen Fuchs, Bad Emstal (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 10/468,923

(22) PCT Filed: Feb. 26, 2002

(86) PCT No.: PCT/EP02/02042

§ 371 (c)(1),
(2), (4) Date: Feb. 2, 2004

(87) PCT Pub. No.: WO02/068022

PCT Pub. Date: Sep. 6, 2002

(65) Prior Publication Data

US 2004/0116856 A1    Jun. 17, 2004

(30) Foreign Application Priority Data

Feb. 26, 2001    (DE) ................ 201 03 363

(51) Int. Cl.
*A61M 5/178*    (2006.01)
(52) U.S. Cl. ............ 604/164.08; 604/110; 604/164.07; 604/192; 604/197
(58) Field of Classification Search ............... 604/187, 604/197, 192, 198, 164, 184, 110, 263
See application file for complete search history.

(56) References Cited

U.S. PATENT DOCUMENTS 4,250,881 A    2/1981    Smith (Continued)

FOREIGN PATENT DOCUMENTS

WO    WO 99/08742    2/1999

(Continued)

OTHER PUBLICATIONS

In the Court of the Commissioner of Patent For the Republic of South Africa, entitled "Supplemental Answering Affidavit", B. Braun Melsungen AG (First Applicant) and B. Braun Medical (Proprietary Limited) (Second Applicant) and Specialized Systems Electro Medical (Proprietary Limited (Respondent). in regards Patent of addition 2001/3937 and an application for infringement thereof. Affidavit of Dennis Bialecki, dated and signed Sep. 1, 2005 (36 pages).

(Continued)

*Primary Examiner*—Manuel Mendez
*Assistant Examiner*—Aamer S. Ahmed
(74) *Attorney, Agent, or Firm*—Christie, Parker & Hale, LLP.

(57) ABSTRACT

The invention relates to a protective device for an injection needle or infusion needle, comprising a needle holder at the proximal end of the needle, on whose shaft a protective element for the needle tip can be moved, said protective element being prevented, by an engagement device between the needle and the protective element, from being moved past the needle tip, and a grip part being provided between the protective element and the needle holder for the purpose of moving or securing the protective element.

68 Claims, 6 Drawing Sheets

U.S. PATENT DOCUMENTS

| | | | |
|---|---|---|---|
| 4,790,828 A | 12/1988 | Dombrowski et al. | |
| 4,929,241 A | 5/1990 | Kulli | |
| 4,944,725 A | 7/1990 | McDonald | |
| 4,952,207 A | 8/1990 | Lemieux | |
| 4,964,854 A | 10/1990 | Luther | |
| 4,978,344 A | 12/1990 | Dombrowski et al. | |
| 4,994,041 A * | 2/1991 | Dombrowski et al. | 604/192 |
| 5,049,136 A | 9/1991 | Johnson | |
| 5,053,017 A | 10/1991 | Chamuel | |
| 5,053,107 A | 10/1991 | Barber, Jr. | |
| 5,120,320 A | 6/1992 | Fayngold | |
| 5,135,504 A | 8/1992 | McLees | |
| 5,215,525 A | 6/1993 | Sturman | |
| 5,215,528 A | 6/1993 | Purdy et al. | |
| 5,217,438 A | 6/1993 | Davis et al. | |
| RE34,416 E | 10/1993 | Lemieux | |
| 5,279,570 A | 1/1994 | Dombrowski et al. | |
| 5,279,591 A | 1/1994 | Simon | |
| 5,300,045 A | 4/1994 | Plassche, Jr. | |
| 5,312,371 A | 5/1994 | Dombrowski et al. | |
| 5,322,517 A | 6/1994 | Sircom et al. | |
| 5,328,482 A | 7/1994 | Sircom et al. | |
| 5,334,158 A * | 8/1994 | McLees | 604/110 |
| 5,344,408 A * | 9/1994 | Partika | 604/192 |
| 5,348,544 A | 9/1994 | Sweeney et al. | |
| 5,419,766 A | 5/1995 | Chang et al. | |
| 5,423,766 A | 6/1995 | Di Cesare | |
| 5,458,658 A | 10/1995 | Sircom | |
| 5,558,651 A | 9/1996 | Crawford et al. | |
| 5,599,310 A | 2/1997 | Bogert | |
| 5,601,536 A | 2/1997 | Crawford et al. | |
| 5,611,781 A | 3/1997 | Sircom et al. | |
| 5,662,610 A | 9/1997 | Sircom | |
| 5,697,907 A | 12/1997 | Gaba | |
| 5,843,048 A * | 12/1998 | Gross | 604/264 |
| 5,882,337 A | 3/1999 | Bogert et al. | |
| 6,004,294 A | 12/1999 | Brimhall et al. | |
| 6,224,569 B1 * | 5/2001 | Brimhall | 604/164.08 |
| 6,287,278 B1 | 9/2001 | Woehr et al. | |
| 6,443,929 B1 | 9/2002 | Kuracina et al. | |
| 6,585,704 B2 | 7/2003 | Luther et al. | |
| 6,595,955 B2 | 7/2003 | Ferguson et al. | |
| 6,616,630 B1 | 9/2003 | Woehr et al. | |
| 6,749,588 B1 | 6/2004 | Howell et al. | |
| 2002/0103463 A1 * | 8/2002 | Luther et al. | 604/263 |
| 2004/0059302 A1 | 3/2004 | Crawford et al. | |

FOREIGN PATENT DOCUMENTS

WO     WO 00/69501     11/2000

OTHER PUBLICATIONS

Office Action dated Jul. 28, 2005. Application No. 10/468,923. Filing Date Feb. 02, 2004, Confirmation No. 2810, Examiner: Aamer S. Ahmed, (22 pages).

* cited by examiner

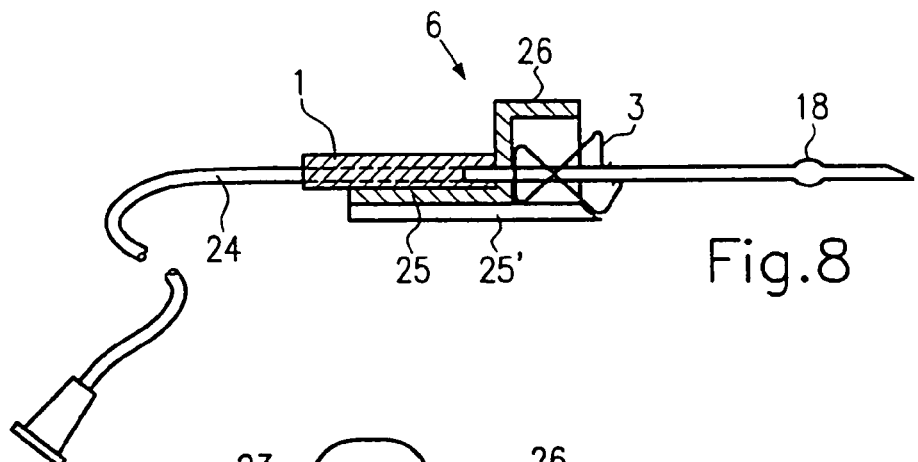
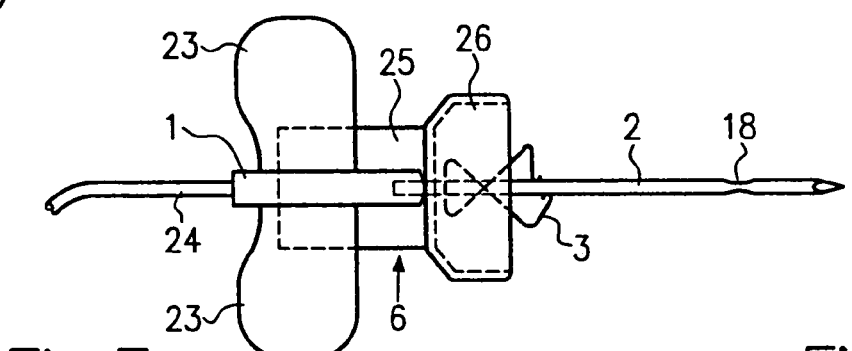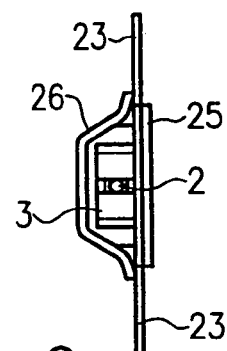
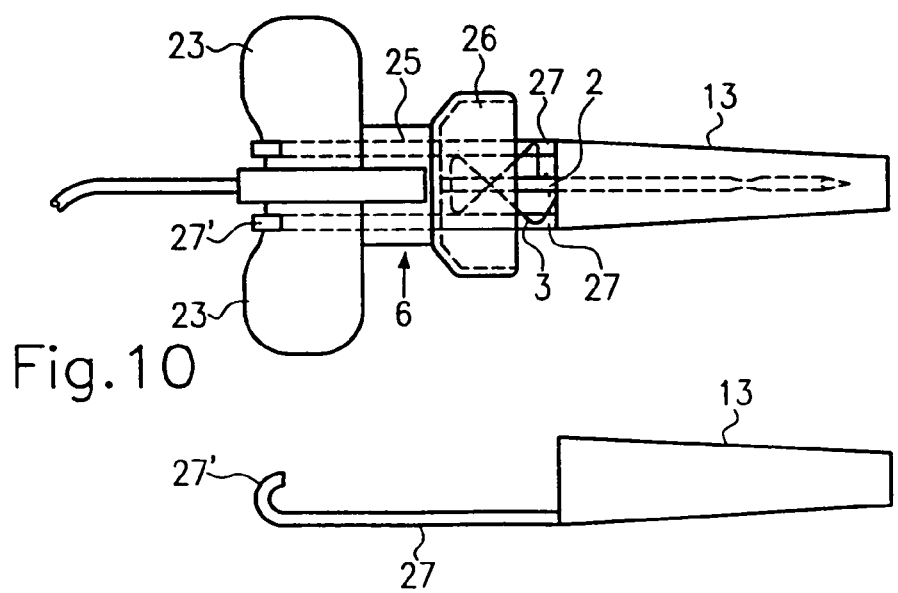

NEEDLE ASSEMBLY WITH PROTECTIVE ELEMENT

CROSS-REFERENCE TO RELATED APPLICATIONS

This application claims priority of International Application No. PCT/EP02/02042, filed Feb. 26, 2002, entitled PROTECTIVE DEVICE FOR AN INJECTION NEEDLE, which claims the benefit of German Application No. 201 03 363.1, filed Feb. 26, 2001, the contents of which are expressly incorporated herein by reference.

SUMMARY OF THE INVENTION

The invention relates to a protective device for an injection needle or infusion needle according to the preamble of claim 1.

A protective device of this kind is known for example from U.S. Pat. No. 4,929,241, in which a relatively small protective element is arranged on the needle and can be moved by a spring from the retracted position to the protection position on the needle tip, with elastic arms of the protective element engaging over the needle tip, while an engagement device on the protective element holds the latter on the needle shaft. Because of the smallness of the protective element, it is difficult to move it by hand on the needle. In addition, the securing spring can only be released when the needle tip lies free, so that a risk of injury cannot be ruled out.

The object of the invention is to design a protective device of the type mentioned at the outset in such a way that actuation by hand is made easier and a risk of injury can be ruled out.

According to the invention, this object is achieved by the features in the characterizing part of claim 1. By virtue of the fact that a grip part for moving the protective element is provided between protective element and needle holder, it is possible, when drawing the needle back by means of the needle holder after an injection, to hold the grip part comfortably with the other hand so that, as a result of the relative movement between needle and grip part, the protective element is moved into the protection position on the needle tip without the small protective element having to be touched with the fingers. A risk of injury can also be ruled out by virtue of the fact that the protective element is brought into the protection position when the needle is being drawn back.

BRIEF DESCRIPTION OF THE DRAWINGS

Illustrative embodiments of the invention are explained in more detail below with reference to the drawings, in which:

FIG. 7 shows an embodiment in conjunction with a needle holder provided with wings;

FIG. 8 shows a cross section through the embodiment according to FIG. 7;

FIG. 9 shows an end view of FIG. 7;

FIG. 10 shows a plan view of an embodiment according to FIG. 7 with needle cap;

FIG. 11 shows a view of the needle cap according to FIG. 10;

DETAILED DESCRIPTION OF THE INVENTION

Figure 1:
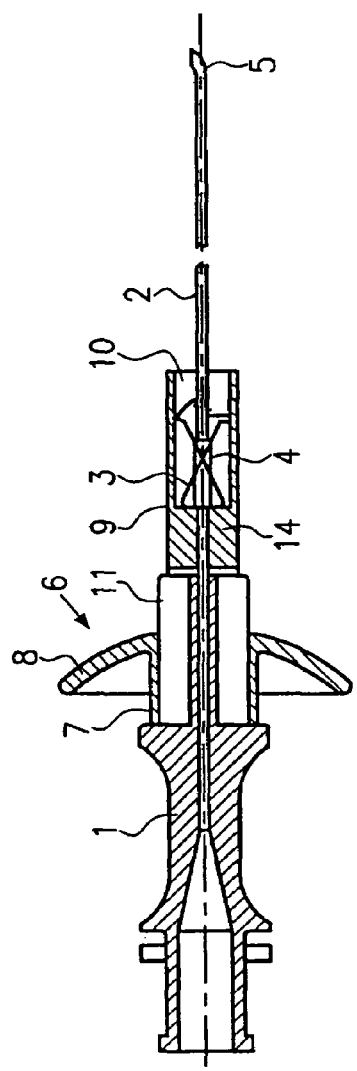
FIG. 1 shows a protective device in longitudinal section.

FIG. 1 shows a needle holder 1 in which a needle 2 is secured. Arranged on the shaft of the needle 2 there is a protective element 3 in the form of a spring clip with intersecting arms. Reference number 4 indicates a sleeve which can be moved with the protective element 3 along the needle shaft. In the illustrative embodiment shown, the tip 5 of the needle is designed with a curve in the manner of an epidural needle or a Huber needle, so that the sleeve 4, which has a smaller diameter than the curve on the needle tip, and, together with it, the protective element 3 and cannot be moved past the needle tip.

Arranged between needle holder 1 and protective element 3 there is a grip part 6 which, at the proximal end, has a hollow cylindrical portion 7 on which a radially protruding shield 8 is formed. On the front face of the shield 8 there is a cylindrical portion 9 whose distal end is hollow. In the standby position according to FIG. 1, the protective element 3 is arranged in the cavity 10 and, by displacement of the grip part 6, can be moved forward to the needle tip 5, while the needle holder 1 is held with the other hand. The angled ends of the intersecting arms of the protective element 3 engage over the needle tip 5, so that injury to operating personnel by the needle tip is prevented.

Figure 2:
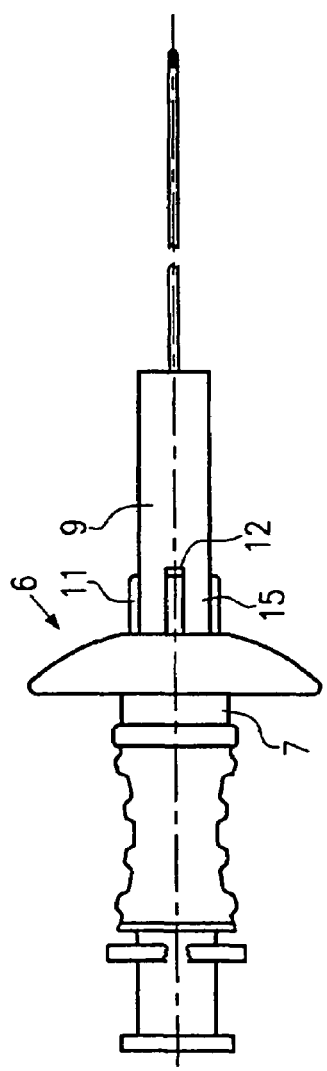
FIG. 2 shows a side view of the embodiment according to FIG. 1.

At the distal end, the needle holder 1 has radially protruding ribs 11 on which the hollow cylindrical portion 7 of the grip part 6 is guided. Between the cylindrical portion 9 of smaller external diameter and the hollow cylindrical portion 7 of greater external diameter, slits 12 are formed in the grip part 6, through which slits 12 the front ends of the ribs 11 of the needle holder 1 protrude radially, as FIG. 2 shows.

The cylindrical portion 9 of the grip part 6 provided with the cavity 10 has a solid cylindrical portion 14 between the slits 12 and the cavity 10, in the central bore of which portion 14 the needle 2 is guided. Between the slits 12 of the grip part 6, the cylindrical portion 9 is connected integrally to the shield 8 and the hollow cylindrical portion 7 via bridges 15.

Figure 4:
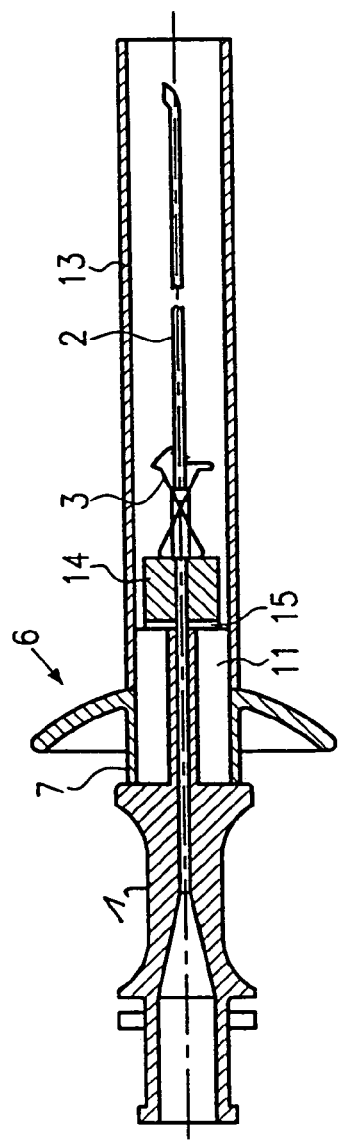
FIG. 4 shows a modified device according to FIGS. 1 and 2 with a needle cap.

These ribs 11 protruding over the outer circumference of the cylindrical portion 9 of the grip part 6 serve for attachment of a needle cap 13, which is shown in FIG. 4. This needle cap 13 is used for storing and handling the device. It can be removed from the needle holder 1 immediately before use of the injection needle, in order to expose the needle, without the grip part 6 and the protective element 3 being moved, because the needle cap 13 is held by the ribs 11 at a radial distance from the portion 9 of the grip part 6.

Because of the smaller diameter at the portion 14 compared to the greater diameter at the ribs 11, the needle cap 13, which consists of a tube section of constant diameter, cannot be positioned incorrectly on the portion 14, but only attached to the ribs 11. This ensures that the needle cap 13 is not inadvertently engaged with a portion of the grip part 6. The needle cap 13 can be produced inexpensively by extrusion of a tube, a section of such a tube forming the needle cap 13.

After removal of the needle cap 13, an injection can be carried out in the standby position according to FIGS. 1 and 2. As the needle is pulled back with one hand on the needle holder 1, the grip part 6 on the portion 7 is held with the other hand, so that the protective element 3 is moved into the protection position on the needle tip as a result of the relative movement between grip part 6 and needle 2. This deployed position of the grip part 6 is illustrated in FIG. 3.

Figure 3:
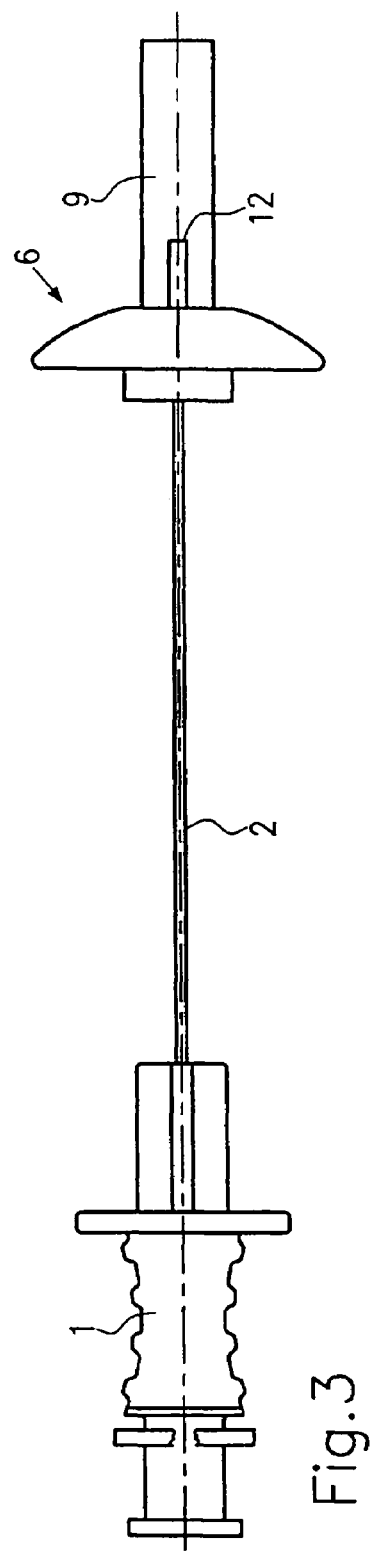
FIG. 3 shows a view of the device according to FIGS. 1 and 2 with the protective element moved to the protection position.

The protective element 3 is arranged loosely in the cavity 10 of the grip part 6, so that the grip part 6 can be easily drawn back from the position in FIG. 3, while the protective element remains in the protection position on the needle tip. The cavity 10 in the cylindrical portion 9 protects the protective element 3 after removal of the needle cap 13.

FIG. 4 shows a preferred embodiment of the grip part 6, the hollow cylindrical portion at the distal end of the grip part 6 being omitted, so that the solid cylindrical portion 14 forms the distal end of the grip part 6. After removal of the needle cap 13 from the ribs 11, the protective element 3 lies free in FIG. 4.

In the embodiment according to FIGS. 1 and 2, the hollow cylindrical portion 7 on the grip part 6 is used to protect the fingers of the hand holding the grip part from touching the needle shaft when the needle is drawn back.

In another configuration of the needle holder 1, this hollow cylindrical portion 7 can be made larger behind the shield 8.

The grip part 6, like the needle holder 1 too, is expediently made of plastic.

Figure 5:
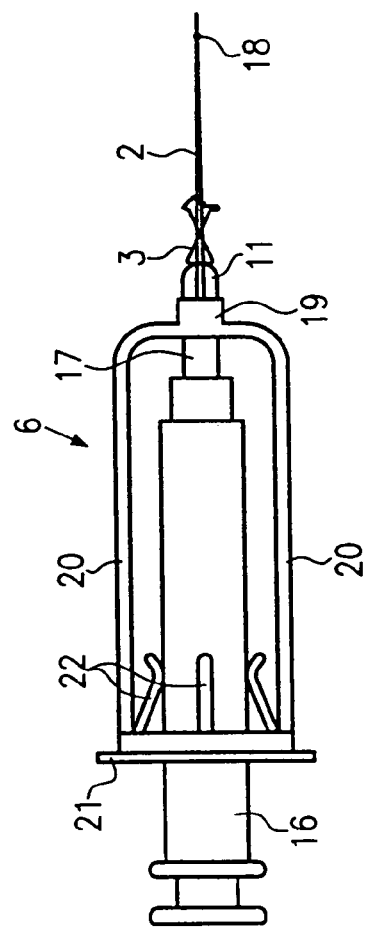
FIG. 5 shows another embodiment of a grip part in conjunction with a syringe.

FIG. 5 shows a modified embodiment of a grip part 6 in combination with a syringe 16 on which an injection needle 2 is secured via a needle holder 17 designed as cannula attachment. In this embodiment, a bead 18 is formed on the outer circumference of the needle, before the needle tip, on which bead 18 the rear wall of the protective element 3 comes to bear in the protection position. Instead of a bead 18, diametrically opposite knob-like projections can be formed by pinching the needle.

The grip part 6 has a cylindrical portion 19 which, in the starting position according to FIG. 5, is guided on the needle holder 17. In the illustrative embodiment shown, two brackets 20 extend from this cylindrical portion 19 in the proximal direction, on diametrically opposite sides, at a distance from the syringe circumference. The ends of these brackets 20 are integrally formed on an annular body 21 from which elastic fingers 22 extend radially inward. The free ends of these elastic fingers 22 lie on the outer circumference of the syringe 16.

Because of the elastic fingers 22 between the grip part 6 and the outer circumference of the syringe 16, the grip part 6 can be used for different sizes of syringe diameter, e.g. syringes with a volume of 1 ml to 10 ml can be fitted into the same grip part. By this means, there is a wide choice of syringes which can be used with the same needle.

In the embodiment according to FIG. 5 too, radially protruding ribs 11 are formed at the front end of the needle holder formed as cannula attachment and these serve as a seat for a needle cap. The protective element 3, whose rear wall protrudes beyond the cross section of the ribs 11, is moved forward into the protection position through the inner circumference of the cylindrical portion 19.

Figure 6:
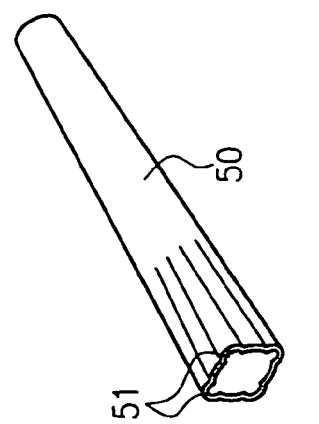
FIG. 6 shows a modified embodiment of the device according to FIG. 5.

FIG. 6 shows an embodiment of the grip part 6 in which, formed on the cylindrical portion 19, there is a further cylindrical portion 9 in whose cavity 10 the protective element 3 is received. As in the embodiment according to FIGS. 1 and 2, axially extending slits are formed between cylindrical portion 19 and portion 9, through which slits the ribs 11 formed on the needle holder or cannula attachment 17 protrude in order to receive the needle cap 13.

Figure 6A:
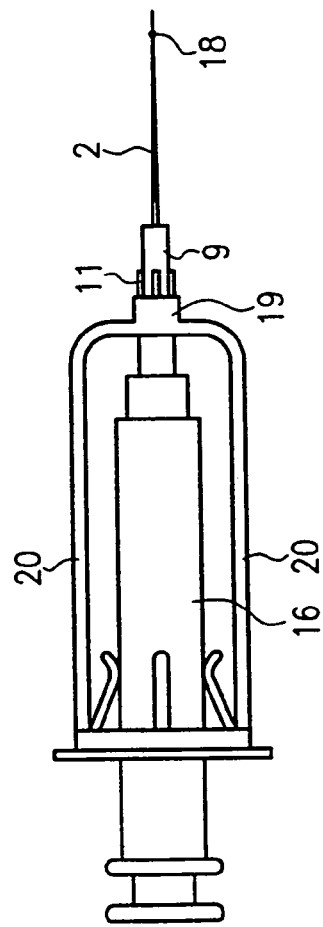

FIG. 6a shows, in a perspective view, a needle cap 50 which is formed by injection-molding and whose distal end can be closed, while the proximal end has, on the inner circumference, flutes or grooves 51 which correspond to the number of ribs 11 and which engage with the ribs 11 when the needle cap is placed on the needle holder 17, so that, by turning the attached needle cap 50, the needle holder 17 can also be turned. A threaded engagement is usually provided between needle holder 17 and syringe 16, so that, by turning the needle cap 50, the needle holder 17 can be screwed onto the syringe 16.

It is customary to draw liquid into the syringe by means of a needle of relatively large diameter and then to replace this needle with a needle having a relatively small diameter, in order to perform an infusion on the patient. In the embodiment according to FIGS. 5 and 6, the needle can be changed without difficulty.

The described design permits actuation with one hand when the syringe content has been injected, the syringe 16 being held with two fingers and the needle being pulled from the patient's skin, while at the same time a finger of the hand bears on the annular body 21 lying at the proximal end.

FIG. 7 shows a plan view of a needle holder 1 which is provided with laterally protruding wings 23 and to which a connection tube 24 is attached. Arranged between the protective element 3 arranged on the needle shaft and the needle holder 1 there is a grip part 6 with a hub-shaped portion 26 which, because of the flat injection angle (FIG. 8), expediently has a surface part 25 for bearing on the patient's skin which, on the bearing side can be provided for example with an adhesive layer for better retention on the skin. A foam material 25' is preferably provided on the bearing side. The hub portion 26 of the grip part 6 protruding from the front end of the surface part 25 at least partially covers the protective element 3. The surface part 25 or the soft bearing part 25' also serves as spacer for keeping the protective element 3 from the patient's skin. In the illustrative embodiment according to FIG. 8, the soft bearing part 25' extends across the surface part 25 under the hub portion 26, so that the protective element 3 does not lie on the patient's skin.

The needle holder 1 provided with wings 23 is used for venous infusions, for which a thin needle is normally used. The wings 23 are relatively large and flexible. They are pressed together if the needle is introduced into the skin at a very flat angle. A protective paper (not shown) applied on the adhesive layer on the bearing surface should not be peeled off until the needle is introduced into the vein. After the needle has been introduced into the vein, the wings 23 are placed flat against the patient's skin and secured with an adhesive tape. The grip part 6 too can be secured by means of an adhesive tape, the hub-shaped portion 26 preventing contact between protective element 3 and adhesive tape. When the needle is drawn back after removal of the adhesive tape from the needle holder, the grip part 6 initially remains in its position with the protective element 3. After the drawn-back needle tip is safely covered by the protective element 3, with the projections 18 on the needle fixing the protective element 3 on the needle tip, the grip part 6 can also be removed from the patient's skin.

FIGS. 7 and 8 show the device in the standby position for insertion of the needle. If the bearing surface 25 provided with an adhesive layer is used on the grip part, this is a passive system.

FIG. 9 shows a view of the grip part 6 from the right in FIG. 7. The wings 23 serve as bearing surface for the needle holder 1 since the infusion needle must remain for a certain time in the inserted position.

FIGS. 10 and 11 show, in a construction according to FIGS. 7 through 9, a needle cap 13 provided with two spaced-apart retaining brackets 27 which are hooked via a curved free end 27' on the wings 23, as FIG. 10 shows. In this embodiment, the proximal end of the needle cap 13 expediently bears on the front end of the protective element 3, as FIG. 10 shows, so that the protective element 3 is held in its standby position.

It is also possible, however, to provide a hub-shaped attachment at the proximal end of the needle cap 13, which attachment bears on the front face of the hub-shaped portion 26.

In the embodiments described, a protective element in the form of a spring clip with intersecting arms is depicted in each case. However, another design of a protective element can also be used in conjunction with the grip part 6.

Figure 12:
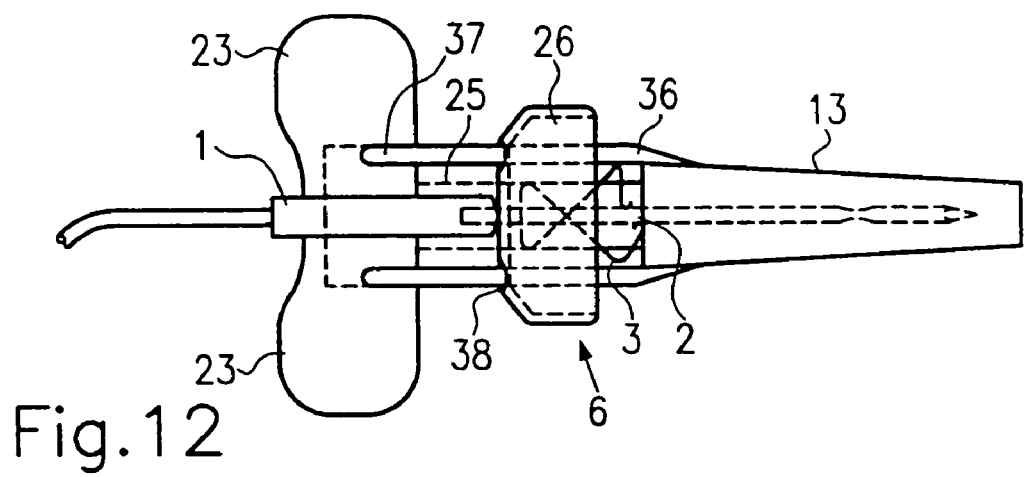
FIG. 12 shows a plan view of an embodiment according to FIG. 7 with a modified needle cap.
Figure 13:
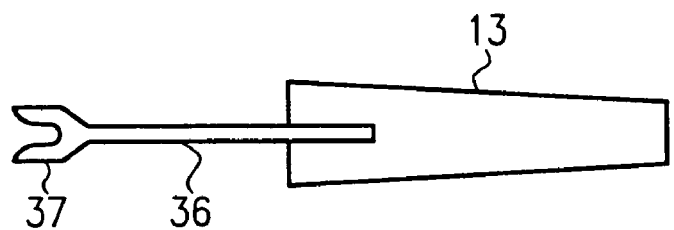
FIG. 13 shows a side view of the needle cap according to FIG. 12.

FIG. 12 shows a further embodiment of the device according to FIGS. 7 through 9. Instead of having the suspension brackets 27, the needle cap 13 is in this case provided on both sides with an extension strut 36 which, at the free end, has a fork-shaped portion 37 for attachment to the wings 23 of the needle holder (FIG. 13). These two spaced-apart struts 36 extend through correspondingly dimensioned openings 38 in the hub portion 26 of the grip part 6, so that the fork-shaped insertion portions 37 can be pulled without difficulty through these openings 38. When the needle cap 13 is taken off, the needle holder 1 is held, and the grip part 6 is not moved.

Figure 14:
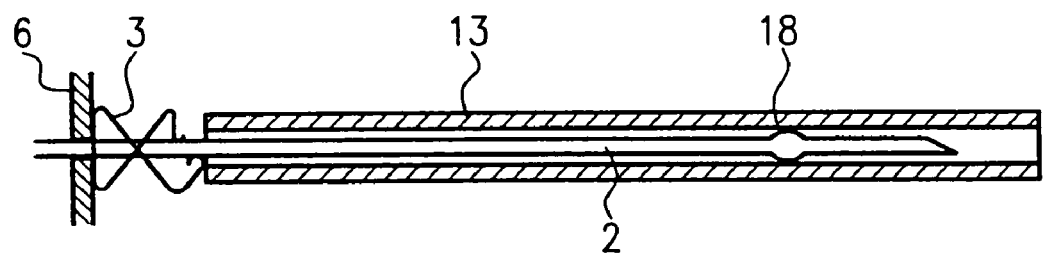
FIG. 14 shows a longitudinal section through a needle cap.

FIG. 14 shows a longitudinal section through a needle cap 13 whose proximal end bears on the protective element 3. The needle cap is of tubular design, and the diameter enlargement 18 on the needle 2, produced by pinching, serves as a spacer for the needle cap 13. Such a needle cap can be produced by extrusion or injection-molding. It is also possible to form, on the inner circumference of the needle cap, a bead or knobs, which bear on the needle shaft and guide the needle substantially concentrically in the needle cap. The needle cap 13 is in this case held on the needle 2 by friction on the bulges 18.

According to a further embodiment, the needle cap, when it has been fitted onto the needle, can be fixed on the needle by mean of heat and pressure or by shrinking.

Figure 15:
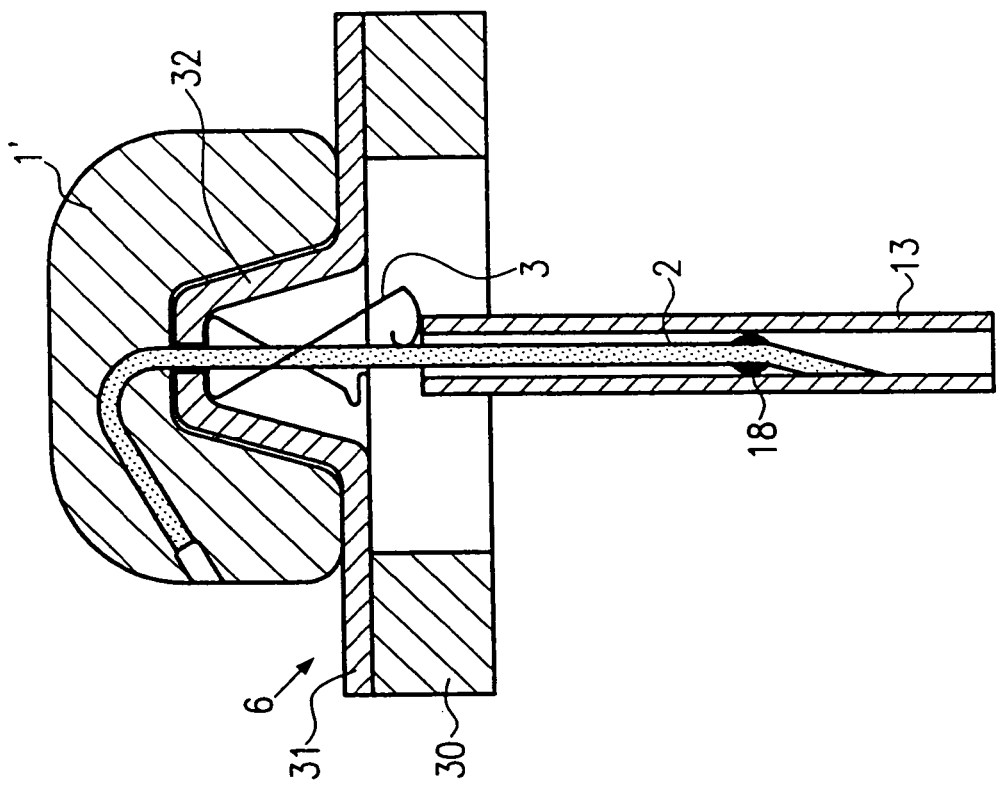
FIG. 15 shows a cross section through another embodiment with a curved needle.

FIG. 15 shows an embodiment in combination with a Huber needle 2 which is held in a needle holder 1' by means of a curved portion and is provided for perpendicular insertion upon injection. Reference number 30 designates a bearing part which is preferably made of foam material and which is provided with an adhesive face for better fixing on the patient's skin. Arranged between the bearing part 30 and the needle holder 1' there is a shield-like grip part 6 which rests on the bearing part via a flange-like area 31 and extends via a pot-shaped middle portion 32 into a corresponding depression in the needle holder 1'. The protective element 3 is arranged in this pot-shaped middle part 32.

When the needle is drawn out, the grip part 6 is held on the bearing part 30, while the needle holder 1' is removed. The protective element 3 is moved toward the needle tip until it comes to rest on the needle bulge 18, while at the same time the two intersecting arms of the protective element 3 engage over the needle tip and cover it. The grip part 6 can be removed from the bearing part 30 or together with the latter. Grip part 6 and bearing part 30 can also be connected to one another via an adhesive layer.

The side walls of the pot-shaped middle part 32 are preferably conical so that the grip part 6 cannot itself be removed but instead only pressed.

FIG. 15 shows a needle cap 13' with a tubular portion from whose proximal end there protrude diametrically opposite wall portions 33 which are inserted via partially circular slits 34 in the flange 31 of the grip part 6 into correspondingly partially circular grooves 35 in the needle holder 1'. The curved wall portions 33 are guided loosely through the curved slits 34 in the flange 31 of the grip part 6 and inserted with a press fit into the grooves 35 of the needle holder 1'.

As in the other embodiments of a needle cap 13, the needle cap 13' in FIG. 15 can also be closed at the distal end.

Figure 16:
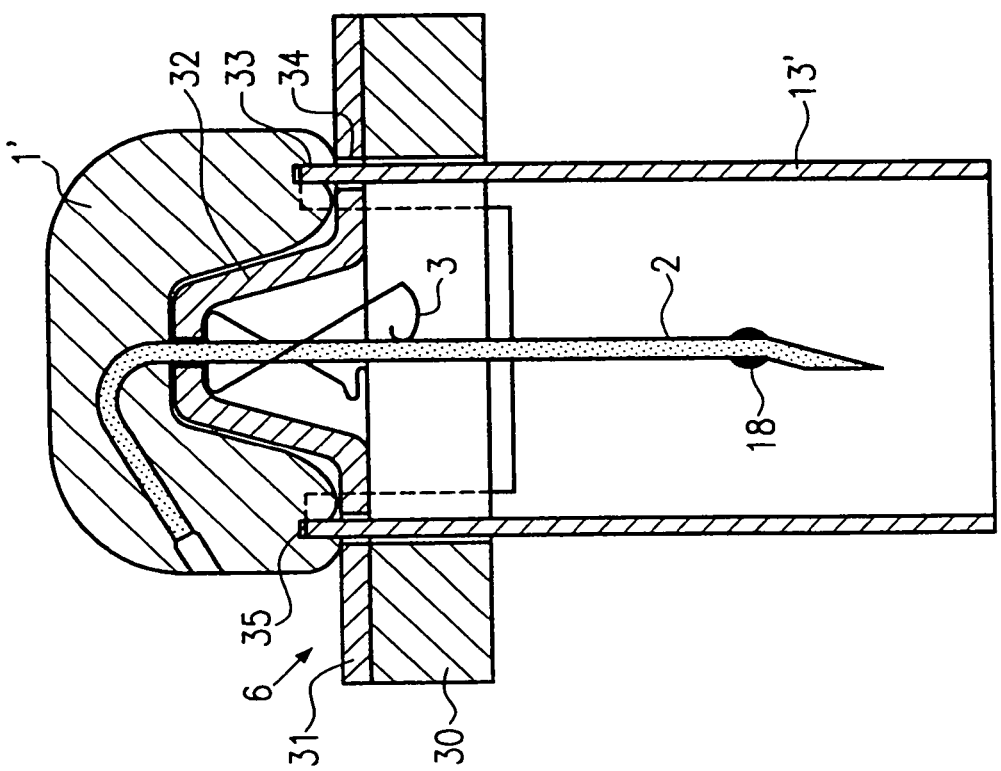
FIG. 16 shows another needle cap in the embodiment according to FIG. 15.
Figure 16A:
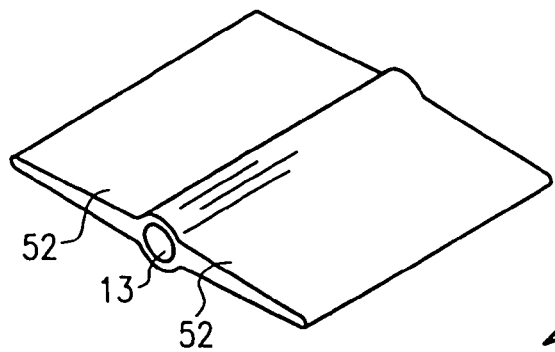

FIG. 16 shows an embodiment with a Huber needle 2 according to FIG. 15, where a needle cap 13 of smaller internal diameter is pushed onto the needle 2. The needle cap corresponds substantially to that of FIG. 14, the needle cap 13 being held on the needle by means of friction at the angled front end. This needle cap 13 in FIG. 16 can be provided with radially protruding and diametrically opposite surface portions 52 through which handling is improved and the tubular needle cap 13 is made more rigid. FIG. 16*a* shows a perspective view of such a needle cap 13 with diametrically opposite surface portions 52.

Figure 17:
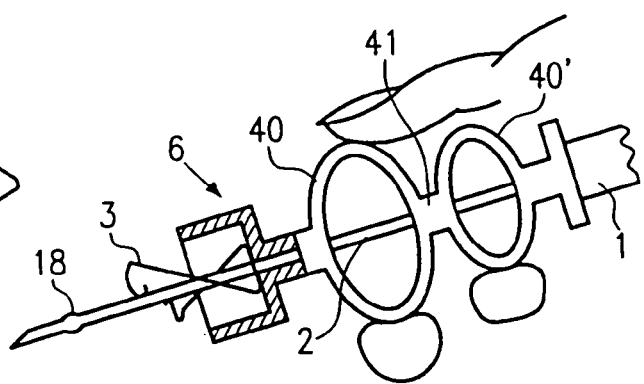
FIG. 17 shows an embodiment with a deformable grip part in the starting position.
Figure 18:
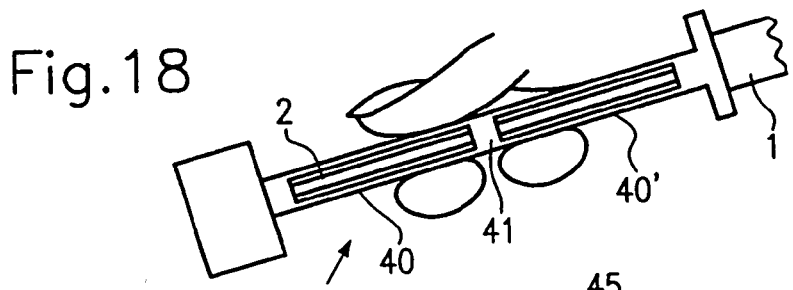
FIG. 18 shows the grip part from FIG. 17 in the extended position.

FIGS. 17 and 18 show an embodiment in which the grip part 6 has a deformable portion by means of which the distal end of the grip part, on which the protective element 3 lies, can be moved in the direction of the protection position on the needle tip by means of the deformable portion being deformed. In the illustrative embodiment according to FIGS. 17 and 18, two pairs of deformable brackets 40 and 40' are formed on the grip part 6 and these can be pressed together by the fingers so that they can be moved from the curved state in FIG. 17 to an extended state in FIG. 18. The two deformable pairs of brackets 40 and 40' are connected to one another by a sleeve portion 41. It is also possible to insert, between the two bracket pairs 40 and 40', an element which, when pressed by the fingers, changes the two deformable brackets 40 and 40' to the extended position according to FIG. 17.

Figure 19:
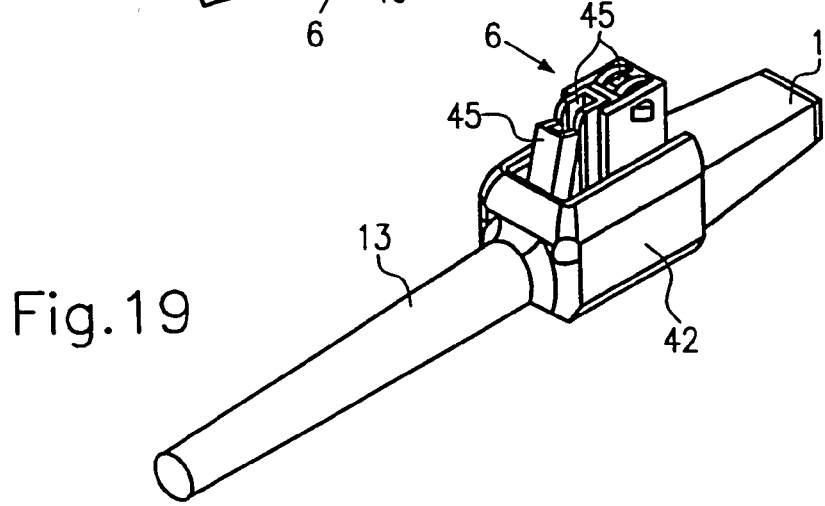
FIG. 19 shows a further embodiment of a deformable grip part in the starting position.
Figure 20:
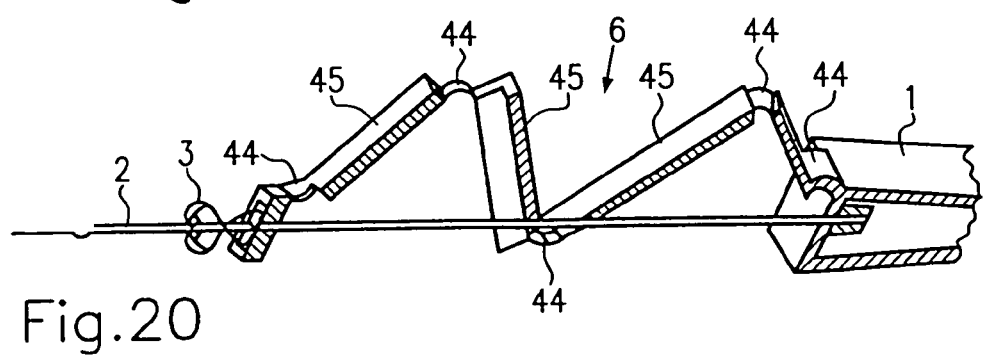
FIG. 20 shows the grip part from FIG. 19 in the deployed position.

FIGS. 19 and 20 show a further embodiment of a deformable grip part 6, FIG. 19 illustrating the grip part in the collapsed state in the standby position. The needle cap 13 is provided at the proximal end with a receiving portion 42 which receives collapsed portions 45 of the grip part 6, which is arranged between needle holder 1 and the protective element 3 (not shown in FIG. 19) arranged in the receiving portion 42.

FIG. 20 shows in schematic representation the grip part 6 in a partially deployed state after the needle cap 13 has been removed and an injection has been carried out. The stiff portions 45 of the grip part 6 which are connected to one another via articulations and hinge portions 44 and which are partially guided on the needle 2 are moved and aligned along the needle, the protective element 3 being pushed forward to the needle tip until it engages with the needle bulge 18 and covers the needle tip.

Compared to the embodiments according to FIGS. 17 through 20, the embodiments according to FIGS. 1 through 16 have the advantage that a greater cannula length is available in the standby position because the protective element 3 lies directly on the needle holder, whereas, in the embodiments according to FIGS. 17 through 20, a more complicated design of the grip part 6 is provided between protective element 3 and needle holder 1, as a result of which the available cannula length is restricted. The embodiment according to FIGS. 19 and 20 is also more advantageous in terms of the length of the available cannula than the embodiment according to FIGS. 17 and 18 because a more compact arrangement is made possible by the folding of the portions 45, as FIG. 19 shows when compared to FIG. 17. Instead of the fold portions in FIG. 20, a scissor mechanism between protective element and needle holder can also be provided in order to accommodate, in a smaller space, elements with which the protective element can be deployed.

Figure 14A:
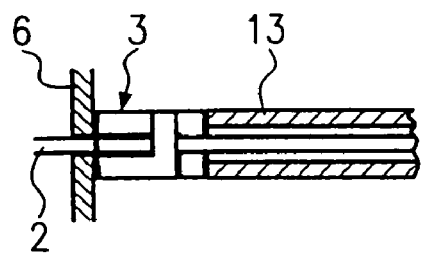

In all the embodiments, the protective element 3 is preferably a needle clip which is made of metal and whose intersecting arms issue from opposite sides of a proximal wall portion having a hole for the passage of the needle, the hole diameter being smaller than the maximum transverse dimension of the needle at the pinch 18, so that the needle clip is held in the protection position on the needle tip by means of the portion 18 of increased diameter. The intersecting arms extending on both sides of the needle 2, as FIG. 14a shows, have, at the distal end, an end portion which is widened to approximately the width of the rear wall and which, in the starting position, lies with elastic pretensioning on the outer circumference of the needle and, on reaching the needle tip, is moved by spring action into the protection position in which the two widened end portions engage over the needle tip. For this purpose, the distal ends of the arms, as the side views show, are slightly offset with respect to one another in the longitudinal direction or the arms are of different lengths, so that it is thus ensured that the two angled end portions of the arms engage over the needle tip. At least on the longer arm, the end portion is curved inward at the free edge in order to ensure that the needle tip is covered even if an attempt is made to push the needle clip back from the protection position on the needle, the inwardly curved end portion hooking onto the needle tip. The needle clip as a whole can be made very compact and only about 7 mm long.

What is claimed is:

1. A hypodermic needle assembly comprising a needle holder holding a portion of the hypodermic needle on an end spaced apart from a needle tip; a protective element comprising two arms and a wall comprising a first wall side and a second wall side positioned at an angle to the two arms and having an opening being slidably mounted on the hypodermic needle; a grip part comprising an interior surface defining an interior cavity and an exterior surface defining a gripping portion; wherein the protective element is disposed, at least in part, within the interior cavity of the grip part and the grip part and the needle holder have portions that overlap when the protective element is in the ready to use position: wherein the grip part is configured to be gripped and slide distally, which separates the grip part from the needle holder, which grip part then moves the protective element to a protective position to protect the needle tip from accidental contact therewith; and wherein the protective element is configured to prevent the grip part from being displaced beyond the needle tip and the grip part is configured to remain axially moveable along at least at portion of the needle relative to the protective element.

2. The hypodermic needle assembly of claim 1, wherein the grip part comprises a proximal end comprising an opening having the hypodermic needle passing therethrough.

3. The hypodermic needle assembly of claim 2, wherein the grip part comprises a tapered wall section.

4. The hypodermic needle assembly of claim 1, wherein the hypodermic needle is a Huber needle or an epidural needle.

5. The hypodermic needle assembly of claim 1, wherein the needle comprises a bead or a crimp.

6. The protective device of claim 5, wherein the bead or the crimp prevents the protective element from being displaced beyond the needle tip.

7. The hypodermic needle assembly of claim 1, wherein the wall and the two arms are integrally formed.

8. The hypodermic needle assembly of claim 1, wherein the grip part comprises at least one slit and the needle holder comprises at least one projection and wherein the at least one projection mates with the at least one slit.

9. The hypodermic needle assembly of claim 1, further comprising a generally cylindrical element contacting both the needle and the protective element.

10. The hypodermic needle assembly of claim 9, wherein the cylindrical element is a sleeve and wherein the sleeve interacts with the needle to delimit distal movement of the protective element off of the needle tip.

11. The hypodermic needle assembly of claim 10, wherein the grip part is moveable proximally following moving the protective element to the protective position.

12. The hypodermic needle assembly of claim 1, wherein the protective element is completely disposed within the interior cavity of the grip part.

13. The hypodermic needle assembly of claim 1, further comprising a needle cap for shielding the needle tip when the hypodermic needle is in the ready position.

14. The hypodermic needle assembly of claim 1, wherein the grip part comprises a flat surface part for resting on a patient's skin.

15. The hypodermic needle assembly of claim 14, wherein the flat surface part is integral with the surface part defining the interior cavity.

16. The hypodermic needle assembly of claim 15, further comprising a needle cap.

17. The hypodermic needle assembly of claim 1, further comprising an axially expandable actuator for moving the grip part distally towards the needle tip.

18. The hypodermic needle assembly of claim 17, wherein the axially expandable actuator is positioned between the grip part and the needle holder.

19. The hypodermic needle assembly of claim 18, wherein the axially expandable actuator comprises a plurality of articulating hinge portions.

20. The hypodermic needle assembly of claim 18, wherein the axially expandable actuator comprises at least one deformable bracket.

21. The hypodermic needle assembly of claim 1, wherein the portions that overlap comprise a tapered wall section of the grip part telescopically engaging a tapered wall section of the needle holder.

22. The hypodermic needle assembly of claim 1, wherein the portions that overlap comprise a generally annular wall section of the grip part telescopically mounted over a generally cylindrical distal portion of the needle holder.

23. The hypodermic needle assembly of claim 1, wherein the portions that overlap comprise a flat surface part of the grip part frictionally contacting a generally cylindrical section of the needle holder.

24. A needle assembly comprising a needle holder holding a portion of a hypodermic needle, the hypodermic needle having a needle tip: a protective element comprising at least one arm attached to and extending from a wall comprising a first wall side and a second wall side and comprising an opening having the hypodermic needle passing therethrough, the protective element being moveable along a portion of the hypodermic needle; a grip part comprising a surface portion defining a cavity and comprising an opening having the hypodermic needle passing therethrough, the surface portion comprising a contact portion on an interior surface adapted to contact a portion of the protective element to move the protective element from a first position on the hypodermic needle to a second position on the hypodermic needle; wherein when the hypodermic needle is in a ready to use position, the grip part receives at least a portion of the protective element inside the cavity and the surface portion surrounds the protective element so that the grip part and the protective element have portions that overlap; and wherein the protective element configured to prevent the grip part from being displaced beyond the needle tip and the grip part is configured to remain axially moveable along at least a portion of the needle relative to the protective element.

25. The needle assembly of claim 24, wherein the at least one arm and the wall are integrally formed.

26. The needle assembly of claim 24, wherein the hypodermic needle comprises a bend proximate the needle tip.

27. The needle assembly of claim 24, further comprising a bead or a crimp proximate the needle tip.

28. The needle assembly of claim 24, further comprising a generally cylindrical element in contact with both the needle and the protective element.

29. The needle assembly of claim 28, wherein the generally cylindrical element engages the needle and remains in contact with the protective element when the protective element moves to the second position.

30. The needle assembly of claim 24, wherein the protective element is completely disposed in the cavity.

31. The needle assembly of claim 24, wherein the portions that overlap comprise a tapered wall section of the grip part surrounding the protective element.

32. The needle assembly of claim 24, wherein the grip part overlaps a portion of the needle holder.

33. The needle assembly of claim 24, further comprising a second arm.

34. A hypodermic needle assembly comprising a needle holder holding a portion of a hypodermic needle, the hypodermic needle comprising a needle tip; a grip part comprising a body section comprising an opening having the hypodermic needle passing therethrough; and a protective element in sliding communication with the hypodermic needle having two arms that intersect when in a ready to use position and which are located proximally of a distal wall for blocking the neddle tip; wherein the grip part is configured to be gripped and move from a proximal position to a distal position on the hypodermic needle, which moves the protective element to the distal position on the hypodermic needle; and wherein the protective element is configured to prevent the grip part from being displaced beyond the needle tip.

35. The hypodermic needle assembly of claim 34, wherein the protective element is positioned within a cavity defined by the grip part.

36. The hypodermic needle assembly of claim 34, further comprising a cylindrical sleeve in contact with both the needle and the protective element.

37. The hypodermic needle assembly of claim 34, wherein the needle comprises a curved portion defining an upstream section positioned at an angle to a downstream section.

38. A hypodermic needle assembly comprising:
(a) a needle hub having a needle attached thereto, the needle comprising a needle shaft, a proximal end, and distal end having a needle tip;
(b) a needle ready-to-use position and a protective position;
(c) a grip part axially movable relative to the needle hub comprising a body section comprising a wall structure comprising an exterior wall surface, an interior wall surface, and an end wall comprising an opening having the needle passing therethrough, the wall structure defining an interior cavity and the exterior wall surface capable of being gripped when in the ready-to-use position;
(d) a tip protector positioned on the needle shaft, is surrounded by and contacts the interior surface of the body section of the grip part, the tip protector comprising a proximal wall comprising a wall surface comprising a width, an integrally formed continuous perimeter defining an opening, at least one arm extending distally of the proximal wall, and a radially extending wall comprising a portion at a distal end biased against a side of the needle shaft, the at least one arm comprising an arm section comprising an arm width having a smaller dimension than the width of the wall surface of the proximal wall; and
(e) wherein when the tip protector is in the protective position, the tip protector remains in the interior cavity of the grip part, covers the needle tip, and is configured to prevent the grip part from being displaced distally off of the needle tip.

39. The hypodermic needle assembly of claim 38, wherein the needle tip comprises a curve section defining an upstream needle section positioned an angle to a downstream needle section.

40. The hypodermic needle assembly of claim 39, further comprising a sleeve positioned on the needle and movable with the tip protector.

41. The hypodermic needle assembly of claim 40, wherein the sleeve abuts the curve section of the needle to limit distal advancement of the tip protector.

42. The hypodermic needle assembly of claim 38, wherein the at least one arm and the proximal wall are integrally formed.

43. The hypodermic needle assembly of claim 38, further comprising a second arm extending distally of the proximal wall.

44. The hypodermic needle assembly of claim 43, wherein the at least one arm and the second arm intersect one another in the ready-to-use position.

45. The hypodermic needle assembly of claim 38, wherein the grip part is made from a plastic material and the tip protector from a metal.

46. The hypodermic needle assembly of claim 38, wherein the body section of the grip part comprises a distal end section extending beyond a distal end of the at least one arm.

47. A hypodermic needle assembly comprising a needle holder at a proximal end of a needle, on whose shaft a protective element for a needle tip can be moved, said protective element prevented by an engagement element, positioned between the needle and the protective element, from being moved past the needle tip;
   a grip part provided between the protective element and the needle holder for moving the protective element, the grip part in use being held in a hand, and as a result of relative movement between the needle and the grip part, the protective element is moved into its protective position on the needle tip without the protective element being touched and with the engagement element being moveable along the needle shaft when the grip part is moved, the grip part being prevented from being removed from the needle;
   wherein the engagement element is a sleeve located on the needle shaft and being movable along the needle shaft; and
   wherein the protective element comprises two arms of different lengths extending from a proximal wall portion, the proximal wall portion having a hole for the passage of the needle from a ready position to a protective position.

48. The hypodermic needle assembly of claim 47, wherein the two arms intersect in the ready position.

49. The hypodermic needle assembly of claim 47, wherein the needle comprises a curve section defining an upstream needle section positioned an angle to a downstream needle section.

50. The hypodermic needle assembly of claim 47, wherein the grip part comprises a body section comprising a distal end section extending beyond a distal end of the protective element.

51. The hypodermic needle assembly of claim 47, wherein the sleeve comprises an outside diameter of smaller dimension than a proximal wall height.

52. The hypodermic needle assembly of claim 51, wherein the protective element is integrally formed.

53. A hypodermic needle assembly comprising a needle holder at a proximal end of a needle comprising a needle tip, on whose shaft a protective element for the needle tip can be moved, said protective element comprising a surface area that overlaps with a surface area on an engagement element to delimit movement of the protective element distally beyond the needle tip;
   a grip part capable of being gripped for moving the protective element from a proximal position on the needle to a distal position on the needle and as a result of relative movement between the needle and the grip part, the protective element is moved into its protection position on the needle tip without the protective element being touched; the grip part comprising a surface area that overlaps with a surface area on the protective element to delimit movement of the grip part distally beyond the needle tip and surrounds a distal end of the protective element;
   wherein the protective element comprises two arms of dissimilar lengths with each arm comprising a radially extending wall for blocking the needle tip;
   wherein the engagement element is moveable along the needle.

54. The hypodermic needle assembly of claim 53, wherein the needle comprises a curve section defining an upstream needle section positioned an angle to a downstream needle section.

55. The hypodermic needle assembly of claim 53, wherein the engagement element is separable from the protective element.

56. The hypodermic needle assembly of claim 53, wherein the protective element is integrally formed.

57. The hypodermic needle assembly of claim 53, wherein the engagement element is positioned between the two arms.

58. The hypodermic needle assembly of claim 53, wherein the engagement element surrounds the needle.

59. A hypodermic needle assembly comprising:
   (a) a needle hub having a needle attached thereto, the needle comprising a needle shaft, a proximal end, and distal end having a needle tip;
   (b) a tip protector positioned on the needle shaft comprising a proximal wall comprising a wall surface comprising a width, an integrally formed continuous perimeter defining an opening, at least one arm extending distally of the proximal wall, and a radially extending wall attached at a distal end of the at least one arm for blocking the needle tip, the at least one arm comprising an arm section comprising an arm width having a smaller dimension than the width of the wall surface of the proximal wall;
   (c) a grip part comprising a body section comprising a wall structure comprising an exterior wall surface, an interior wall surface, and an end wall comprising an opening having the needle passing therethrough, the wall structure defining an interior cavity and the exterior wall surface capable of being gripped;
   (d) the tip protector being positioned in the interior cavity of the grip part, the grip part surrounding the tip protector, and the grip part comprising a portion extending distally of the tip protector; and
   (e) wherein the tip protector is configured to prevent the grip part from being displaced distally off of the needle tip.

60. The hypodermic needle assembly of claim 59, wherein the needle tip comprises a curve section defining an upstream needle section positioned an angle to a downstream needle section.

61. The hypodermic needle assembly of claim 60, further comprising a sleeve positioned on the needle and movable with the tip protector.

62. The hypodermic needle assembly of claim 59, wherein the proximal wall of the rip protector is moveable relative to the end wall of the grip part.

63. The hypodermic needle assembly of claim 59, wherein the at least one arm and the proximal wall are integrally formed.

64. The hypodermic needle assembly of claim 59, further comprising a second arm extending distally of the proximal wall.

65. The hypodermic needle assembly of claim 64, wherein the at least one arm and the second arm intersect one another in a ready-to-use position, prior to being moved to block the needle tip.

66. The hypodermic needle assembly of claim 59, wherein the grip part is made from a plastic material and the tip protector from a metal.

67. The hypodermic needle assembly of claim 59, wherein the proximal wall of the tip protector is not mechanically engaged to the grip part.

68. The hypodermic needle assembly of claim 59, wherein the tip protector blocks the needle tip in the absence of a coil spring.

* * * * *

UNITED STATES PATENT AND TRADEMARK OFFICE
CERTIFICATE OF CORRECTION

PATENT NO. : 7,214,211 B2
APPLICATION NO. : 10/468923
DATED : May 8, 2007
INVENTOR(S) : Woehr et al.

It is certified that error appears in the above-identified patent and that said Letters Patent is hereby corrected as shown below:

| | |
|---|---|
| Column 7, line 66, Claim 1 | Delete "position:", Insert --position;-- |
| Column 8, line 6, Claim 1 | Delete "at portion", Insert --a portion-- |
| Column 9, line 9, Claim 24 | Delete "tip:", Insert --tip;-- |
| Column 9, line 26, Claim 24 | After "element", Insert --is-- |
| Column 9, line 61, Claim 34 | Delete "neddle", Insert --needle-- |
| Column 10, line 12, Claim 38 | After "needle", Insert --in a-- |
| Column 10, line 41, Claim 39 | After "positioned", Insert --at-- |
| Column 11, line 25, Claim 49 | After "positioned", Insert --at-- |
| Column 11, line 61, Claim 54 | After "positioned", Insert --at-- |
| Column 12, line 37, Claim 60 | After "positioned", Insert --at-- |

UNITED STATES PATENT AND TRADEMARK OFFICE
CERTIFICATE OF CORRECTION

PATENT NO. : 7,214,211 B2
APPLICATION NO. : 10/468923
DATED : May 8, 2007
INVENTOR(S) : Woehr et al.

It is certified that error appears in the above-identified patent and that said Letters Patent is hereby corrected as shown below:

Column 12, line 43, Claim 62          Delete "rip",
                                      Insert --tip--

Signed and Sealed this

Eighteenth Day of March, 2008

JON W. DUDAS
*Director of the United States Patent and Trademark Office*